United States Patent
Whisenant et al.

(10) Patent No.: US 7,799,023 B2
(45) Date of Patent: Sep. 21, 2010

(54) COMPLIANT ELECTRODE FOR PATENT FORAMEN OVALE CLOSURE DEVICE

(75) Inventors: Brian K. Whisenant, Salt Lake City, UT (US); Clark C. Davis, Holladay, UT (US); Daryl R. Edmiston, Draper, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 917 days.

(21) Appl. No.: 11/534,953

(22) Filed: Sep. 25, 2006

(65) Prior Publication Data

US 2008/0215085 A1    Sep. 4, 2008

Related U.S. Application Data

(60) Provisional application No. 60/720,913, filed on Sep. 26, 2005.

(51) Int. Cl.
*A61B 18/18*    (2006.01)
(52) U.S. Cl. .......................................... 606/41; 606/50
(58) Field of Classification Search .................. 606/41, 606/45–48, 50
See application file for complete search history.

(56) References Cited

U.S. PATENT DOCUMENTS

| | | | |
|---|---|---|---|
| 5,545,200 A * | 8/1996 | West et al. | 607/122 |
| 6,050,992 A * | 4/2000 | Nichols | 606/41 |
| 6,063,082 A * | 5/2000 | DeVore et al. | 606/45 |
| 6,463,332 B1 | 10/2002 | Aldrich | |
| 6,645,198 B1 | 11/2003 | Bommannan et al. | |
| 6,805,129 B1 | 10/2004 | Pless et al. | |
| 6,908,464 B2 | 6/2005 | Jenkins et al. | |
| 6,939,348 B2 | 9/2005 | Malecki et al. | |
| 6,944,490 B1 | 9/2005 | Chow | |
| 6,970,742 B2 | 11/2005 | Mann et al. | |
| 7,165,552 B2 | 1/2007 | Deem et al. | |
| 7,186,251 B2 | 3/2007 | Malecki et al. | |
| 7,257,450 B2 | 8/2007 | Auth et al. | |
| 7,293,562 B2 | 11/2007 | Malecki et al. | |
| 7,367,975 B2 | 5/2008 | Malecki et al. | |
| 2004/0193147 A1* | 9/2004 | Malecki et al. | 606/32 |
| 2004/0230185 A1* | 11/2004 | Malecki et al. | 606/2 |
| 2004/0243122 A1 | 12/2004 | Auth et al. | |
| 2004/0260278 A1 | 12/2004 | Anderson et al. | |
| 2004/0267191 A1* | 12/2004 | Gifford et al. | 604/22 |
| 2005/0021016 A1 | 1/2005 | Malecki et al. | |

(Continued)

FOREIGN PATENT DOCUMENTS

WO    WO/99/18871    4/1999

*Primary Examiner*—Lind C Dvorak
*Assistant Examiner*—Benjamin Lee
(74) *Attorney, Agent, or Firm*—Holland & Hart, LLP

(57) ABSTRACT

A medical device for use in delivering RF energy to a tissue opening is disclosed. In one embodiment, the medical device comprises a compliant electrode. The compliant electrode can include a shape memory material, such as NITINOL, to facilitate the electrode having at least one relaxed orientation. The electrode can be deployed from a delivery shaft inside the left atrium, for example, of a heart through the delivery shaft. The electrode can be configured to substantially conform to the tissue proximate the tissue opening. After energy is applied to the tissue between the left and right electrodes, the left electrode can be removed from the left atrium by being received back into the delivery shaft and the delivery shaft thereafter removed from the opening.

7 Claims, 6 Drawing Sheets

U.S. PATENT DOCUMENTS

| | | | |
|---|---|---|---|
| 2005/0033288 A1 | 2/2005 | Auth et al. | |
| 2005/0034735 A1 | 2/2005 | Deem et al. | |
| 2005/0080406 A1 | 4/2005 | Malecki et al. | |
| 2005/0119647 A1 | 6/2005 | He et al. | |
| 2005/0131401 A1 | 6/2005 | Malecki et al. | |
| 2005/0131460 A1 | 6/2005 | Gifford et al. | |
| 2005/0192627 A1* | 9/2005 | Whisenant et al. | 606/213 |
| 2005/0192654 A1 | 9/2005 | Chanduszko et al. | |
| 2006/0027241 A1 | 2/2006 | Malecki et al. | |
| 2006/0074410 A1 | 4/2006 | Malecki et al. | |
| 2006/0079870 A1 | 4/2006 | Barry | |
| 2006/0241581 A1 | 10/2006 | Malecki et al. | |
| 2006/0241582 A1 | 10/2006 | Malecki et al. | |
| 2006/0241583 A1 | 10/2006 | Malecki et al. | |
| 2006/0241584 A1 | 10/2006 | Malecki et al. | |
| 2006/0247612 A1 | 11/2006 | Malecki et al. | |
| 2006/0271030 A1 | 11/2006 | Francis et al. | |
| 2006/0271040 A1 | 11/2006 | Horne et al. | |
| 2006/0271089 A1 | 11/2006 | Alejandro et al. | |
| 2006/0276779 A1 | 12/2006 | Malecki et al. | |
| 2006/0276846 A1 | 12/2006 | Malecki et al. | |
| 2007/0010806 A1 | 1/2007 | Malecki et al. | |
| 2007/0044811 A1 | 3/2007 | Deem et al. | |
| 2007/0078485 A1 | 4/2007 | Deem et al. | |
| 2007/0088355 A9 | 4/2007 | Auth et al. | |
| 2007/0093804 A1 | 4/2007 | Kaveckis et al. | |
| 2007/0093805 A1 | 4/2007 | Auth et al. | |
| 2007/0100324 A1 | 5/2007 | Tempel et al. | |
| 2007/0106214 A1 | 5/2007 | Gray et al. | |
| 2007/0112347 A1 | 5/2007 | Malecki et al. | |
| 2007/0123824 A1 | 5/2007 | Kaveckis | |
| 2007/0123851 A1 | 5/2007 | Alejandro et al. | |
| 2007/0123852 A1 | 5/2007 | Deem et al. | |
| 2007/0203479 A1 | 8/2007 | Auth et al. | |
| 2007/0287999 A1 | 12/2007 | Malecki et al. | |
| 2008/0009859 A1 | 1/2008 | Auth et al. | |
| 2008/0033425 A1 | 2/2008 | Davis et al. | |

* cited by examiner

COMPLIANT ELECTRODE FOR PATENT FORAMEN OVALE CLOSURE DEVICE

CROSS-REFERENCE TO RELATED APPLICATIONS

This application claims benefits from U.S. Provisional Patent Application, Ser. No. 60/720,913 filed on Sep. 26, 2005 entitled, COMPLIANT ELECTRODE FOR PFO CLOSURE DEVICE, the contents of which are hereby incorporated herein by reference.

BACKGROUND OF THE INVENTION

1. The Field of the Invention

The present invention relates generally to implanting medical devices within a patient. More particularly, the present invention relates to the field of patent foramen ovale ("PFO") closure devices.

2. The Relevant Technology

FIGS. 1A-1C depict various views of a heart. Heart 10 is shown in a cross-section view in FIG. 1A. In a normal heart, the right atrium 30 receives systemic venous blood from the superior vena cava 15 and the inferior vena cava 25 and then delivers the blood via the tricuspid valve 35 to the right ventricle 60. However, in heart 10, there is a septal defect between right atrium 30 and left atrium 40 of a patient's heart which is referred to as a patent foramen ovale ("PFO"). PFO is a birth defect that occurs when an opening between the upper two chambers of the heart fail to close after birth to a lesser or greater degree. This birth defect is sometimes also known as a "hole in the heart."

Other problems with this condition are that a blood clot may travel freely between the left or right atria of the heart, and end up on the arterial side. This could allow the clot to travel to the brain, or other organs, and cause embolization, or even a heart attack. These and other similar defects (septal or otherwise), where some tissue needs to be closed to function properly include the general categories of atrial septal defects ("ASDs"), ventricular septal defects ("VSCs") and patent ductus arterosus ("PDA"), and so forth.

The PFO, which is an open flap on the septum between the heart's right and left atria, is generally identified at 50. In a normal heart, left atrium 40 receives oxygenated blood from the lungs via pulmonary arteries 75 and then delivers the blood to the left ventricle 80 via the bicuspid valve 45. However, in heart 10 some systemic venous blood also passes from right atrium 30 through PFO 50, mixes with the oxygenated blood in left atrium 40 and then is routed to the body from left ventricle 80 via aorta 85.

During fetal development of the heart, the interventricular septum 70 divides right ventricle 60 and left ventricle 80. In contrast, the atrium is only partially partitioned into right and left chambers during normal fetal development as there is a foramen ovale. When the septum primum 52 incompletely fuses with the septum secundum 54 of the atrial wall, the result is a PFO, such as the PFO 50 shown in FIGS. 1A-1C, or an atrial septal defect referred to as an ASD.

FIG. 1C provides a view of the crescent-shaped, overhanging configuration of the typical septum secundum 54 from within right atrium 30. Septum secundum 54 is defined by its inferior aspect 55, corresponding with the solid line in FIG. 1C, and its superior aspect 53, which is its attachment location to septum primum 52 as represented by the phantom line. Septum secundum 54 and septum primum 52 blend together at the ends of septum secundum 54; these anterior and posterior ends are referred to herein as "merger points" and are respectively identified at 56a and 56p. The length of the overhang of septum secundum 54, the distance between superior aspect 53 and inferior aspect 55, increases towards the center portion of the septum secundum 54 as shown.

A tunnel 58 is defined by portions of septum primum 52 and septum secundum 54 between the merger points 56a and 56p which have failed to fuse. The tunnel 58 is often at the apex of the septum secundum 54 as shown. When viewed within right atrium 30, the portion of septum secundum 54 to the left of tunnel 58, which is referred to herein as the posterior portion 57p of the septum secundum 54, is longer than the portion of the septum secundum 54 to the right of tunnel 58, which is referred to herein as the anterior portion 57a of the septum secundum 54. In addition to being typically longer, the left portion also typically has a more gradual taper than the right portion, as shown. The area defined by the overhang of the anterior portion 57a of septum secundum 54 and the septum primum 52 and extending from the anterior merger point 56a toward tunnel 58 is an anterior pocket 59a. Similarly, the area defined by the overhang of the posterior portion 57p of septum secundum 54 and the septum primum 52 and extending from the posterior merger point 56p toward tunnel 58 is a posterior pocket 59p.

Conventional treatments for PFO (and related conditions), have generally involved invasive surgery, which presents a different, new set of risks to a patient. Although there are some less invasive treatments for PFO, these have typically been less efficient at closing the PFO opening than techniques involving invasive surgery. Accordingly, there is a continuing need for improved methods and devices for closing the PFO opening. In particular, there is a need for improved methods and devices for deploying PFO closure anchors in a patient.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

BRIEF SUMMARY OF THE DISCLOSURE

Figure 1A:
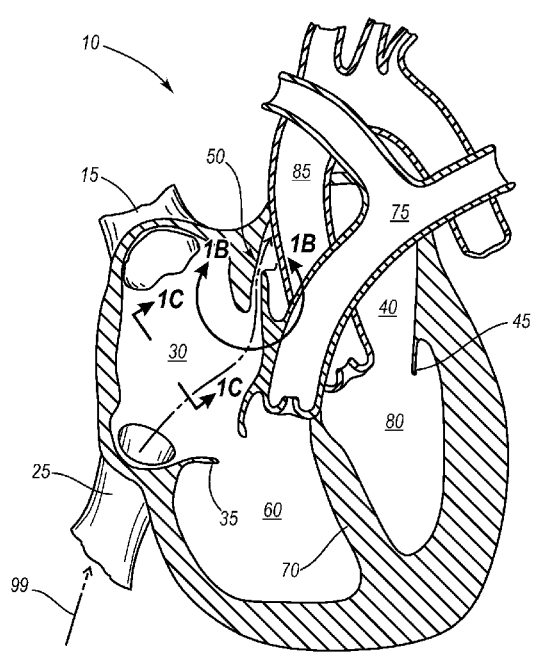
FIG. 1A is a cross-sectional view of a heart.

The invention relates to a medical device for reducing the size of an internal tissue opening utilizing energy, such as radio frequency energy. In one embodiment, the medical device can include a left electrode having a plurality of arms trained to a predetermined orientation. The arms can transition from a constrained orientation to a relaxed orientation, i.e., predetermined orientation, during deployment and/or use of the medical device. The flexibility of the arms and resultant increased surface contact of the electrode with the tissue adjacent to, around, and/or associated with the PFO can increase the effectiveness of a "tissue weld" as energy is applied between the left electrode positioned against a left atrial wall of a heart and a right electrode positioned against the right atrial wall of the heart.

In one embodiment, the arms can include a shape memory material, such as NITINOL, such that the arms can be deformed and will thereafter return to their predetermined, trained, or relaxed orientation. As such, the arms can be configured to be received back into a delivery shaft after the "tissue weld" and the delivery shaft can be removed from the opening. In this manner, the left electrode can be removed from the left atrium of the heart with minimal disturbance of the tissue weld.

The arms can be configured so as to provide coverage of a portion of the tissue wall proximate to the internal tissue opening, such as, but not limited to, a PFO. For example, the arms can be configured to be compliant and exhibit a nonlinear force versus deflection characteristic. The nonlinear force versus deflection characteristic is such that as the plurality of arms become substantially coplanar, the stiffness of the electrode increases through the inter-contacting of the plurality of arms. As the stiffness of the electrode increases, the likelihood that the plurality of arms will pull through an internal tissue opening is reduced. In this manner, the proportion of arm that is in contact with the tissue proximate to the opening is increased.

Various features can be implemented to facilitate placement of the left electrode against the atrial wall of the left atrium. For example, the arms can include a ball portion at the distal tip of each of the arms to reduce the likelihood of the arms inadvertently puncturing the heart. Also, the arms can include a hook positioned in the distal ends of each of the arms to engage a loop portion of a different arm.

These and other objects and features of the present invention will become more fully apparent from the following description and appended claims, or may be learned by the practice of the invention as set forth hereinafter.

DETAILED DESCRIPTION OF THE INVENTION

The present invention extends to systems, methods, and apparatus for a device that is suitable for reducing the size of an internal tissue opening. By way of explanation, the devices disclosed herein can be used for any internal tissue opening, although frequent reference is made herein to closing a PFO opening of a heart tissue using a right atrial anchor and a left atrial anchor for purposes of simplicity. Accordingly, it will be understood that references to PFO openings are not limiting of the invention.

In the following description, numerous specific details are set forth in order to provide a thorough understanding of the present invention. It will be obvious, however, to one skilled in the art that the present invention may be practiced without these specific details. In other instances, well-known aspects of PFO closure devices or medical devices in general have not been described in particular detail in order to avoid unnecessarily obscuring the present invention. In addition, it is understood that the drawings are diagrammatic and schematic representations of certain embodiments of the invention, and are not limiting of the present invention nor are they necessarily drawn to scale.

Illustrative embodiments of the invention relate to delivering radio frequency or RF energy to the septal wall of the heart to treat a defect known as a patent foramen ovale (PFO). In order to treat this type of defect it is desirable to have an electrode system that holds the walls of the flap-like defect together while energy is applied to "weld" the defect closed, i.e. damage the tissue to stimulate tissue growth in the area.

In one embodiment, the medical device can include an electrode configured to increase the effectiveness of the tissue weld. The effectiveness of the tissue weld can be increased by configuring the electrode to contact, and in some instances conform with, the tissue of the atrium proximate the opening of the PFO. Furthermore, the electrode can be configured to be collapsible to a small cross section to remove the electrode from the welded tissue opening without substantially interfering with the new weld.

In one embodiment, the electrode can include a plurality of arms trained to a predetermined orientation. The plurality of arms can include a shape memory material, such as NITINOL, which can be trained to orient themselves in a predetermined shape. The plurality of arms can be configured to be straightened as they are received into a delivery shaft, and then assume their predetermined shape as they are extended from the delivery shaft. Stated another way, the arms can be set with a relaxed orientation that is desirable for tissue contact or conformance; the arms being biased to return to the relaxed orientation when the arms are in the constrained orientation within the delivery shaft.

As such, as used herein, relaxed orientation refers to the predetermined or trained shape of the material; constrained orientation refers to an orientation other than the relaxed orientation, such as, for example, when an arm is forced into a shape different than the shape of the relaxed orientation. For example, the arms can be trained to include one or more curves or the arms can be trained to be substantially straight. Furthermore, the arms can be trained to have multiple relaxed orientations, wherein the relaxed orientations are dependent upon a characteristic, such as temperature. In this example, certain temperature ranges can correspond to a specific relaxed orientation. Another example can include the arms having a substantially straight relaxed orientation during a first temperature range and having a curved relaxed orientation, such as illustrated in any of FIGS. 2 and 6-9A, during a second temperature range. Also, it will be appreciated that the entire arm can be trained, or a portion or multiple portions of the arm can be trained.

The plurality of arms can be configured so as to provide coverage of a portion of the arterial wall proximate to the internal tissue opening, such as a PFO. For example, the plurality of arms can be configured with a nonlinear force versus deflection characteristic. The nonlinear force versus deflection characteristic results in increased stiffness of the electrode as the plurality of arms become substantially coplanar. As the stiffness of the electrode increases due to the inter-connection of the plurality of arms, the likelihood that the plurality of arms will pull through an internal tissue opening is reduced. In this manner, a practitioner can apply pressure to the electrode thus resulting is the plurality of arms being positioned against the opening of the PFO. In a similar manner, the plurality of arms can be configured to be compliant. The compliancy of the plurality of arms can increase the density of the plurality of arms in the proximity of the internal tissue opening.

The plurality of arms can include various other features to facilitate placement of the electrode against the arterial wall of the atrium. For example, the plurality of arms can include a ball portion at the distal tip of the plurality of arms. The ball portion can be configured to reduce the likelihood of the plurality of arms inadvertently puncturing the tissue of the arterial wall.

Figure 1B:
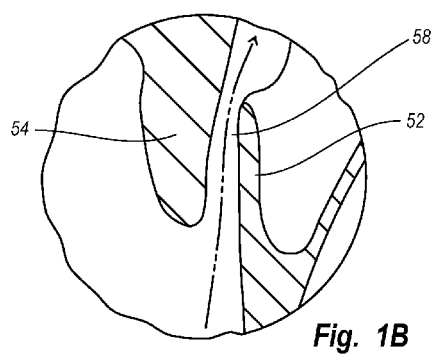
FIG. 1B is an enlarged cross-section view of septum primum and the septum secundum and a PFO tunnel between the septum primum and the septum secundum.
Figure 1C:
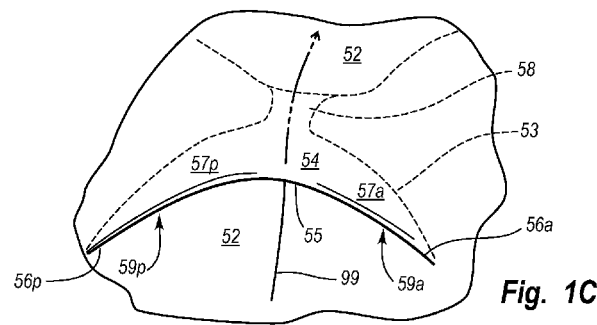
FIG. 1C is a perspective view of the septum secundum with the tunnel and the septum primum shown in phantom.
Figure 2:
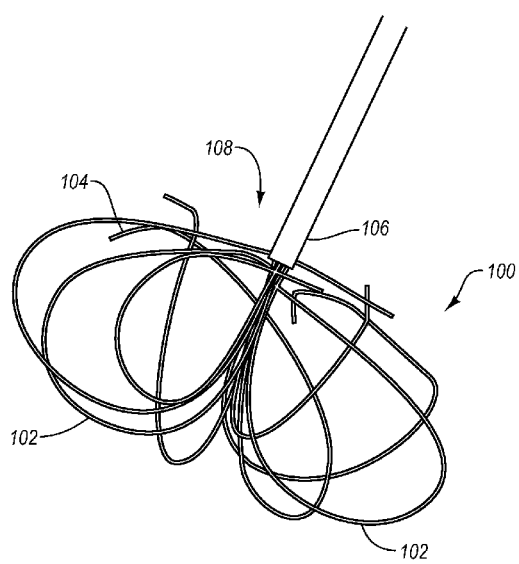
FIG. 2 is a perspective view of an electrode according to one configuration of the present invention.

With reference now to the illustrated embodiments, FIG. 2 is a perspective view of a deployed electrode 100 in a relaxed orientation. The following discussion is made with respect to a left electrode that can be disposed in the left atrium 40 of the heart 10 (FIG. 1). It will be understood, however, that the features and functions of the electrode can also be adapted for a right electrode positionable within the right atrium 30 (FIG. 1) or in any other lumen of the patient.

In the illustrated embodiment, electrode 100 includes one or more arms 102 extending radially from an axial tubular housing 106. Arms 102 can extend radially from housing 106 due to arms 102 being trained to have the illustrated relaxed orientation. For example, in the illustrated embodiment, arms 102 can be trained to extend radially from housing 106 and then curve back around so as to form a bulb shape with an optionally partially flattened bottom as shown in FIG. 2A.

Housing 106 can be configured to secure proximal ends of arms 102 together such that movement of housing 106 can result in movement of arms 102. Alternatively, housing 106 can be configured so as to enable arms 102 to move through housing 106 such that arms 102 can move relative to housing 106. Furthermore, housing 106 can be configured such that those portions of respective arms 102 which extend out from housing 106 are trained portions of arms 102; however, housing 106 can be configured to house both trained and/or non-trained portions of arms 102. Housing 106 can be configured to facilitate deployment of electrode 100, as will be discussed more fully herein.

In one embodiment, electrode 100 can include from 4 to 10 arms made of a Shape Memory Material (SMM), such as superelastic NITINOL. NITINOL is a nickel titanium alloy that belongs to a class of materials called Shape Memory Alloys (SMA), which in turn belongs to the broader class of SMM. SMMs have a shape memory effect in which they can be made to remember a particular shape. Once the material has been made to remember a particular shape, i.e. set or trained, the material can be bent out of shape and then upon unloading from strain or heating the material will return to its set, relaxed or trained orientation. While various methods of setting or training a material are known, one way in which material can be trained is through a heating process. In one embodiment, arms 150, which comprise NITINOL materials, can be trained to remember a certain shape, can then be straightened, for example in a shaft, catheter or other tube, and then released from the catheter or tube to return to the trained shape. Other SMM's can include a magnetic shape memory alloy which can change their shape in response to a change in a magnetic field. Furthermore, the SMM can be a shape memory polymer, such as a "smart plastic" which can hold different shapes at different temperatures.

Arms 102 can be wrapped, coated, or filled with a biocompatible radiopaque material such as platinum to enhance the visibility of the device under fluoroscopy. Furthermore, arms 102 can include marker bands attached thereto to enhance visibility under fluoroscopy. The distal ends of the arms 102 may have a ball formed at the tip to reduce the possibility of an arm inadvertently perforating the heart. An example of a ball 224 is shown with respect to arm 220 of FIG. 9B. Ball 224 can also be configured to provide enhanced visibility under fluoroscopy.

Figure 3:
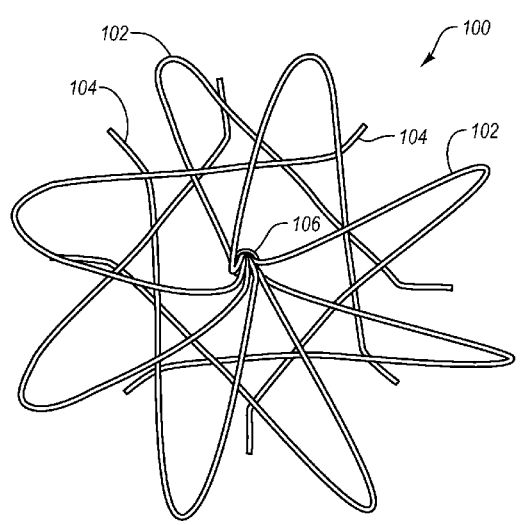
FIG. 3 is a top view of the electrode of FIG. 2.

With reference now to FIG. 3, arms 102 can include a hook 104 at the distal end of respective arms 102. Hooks 104 can be configured to engage one or more different arms 102 so as to inter-connect arms 102. Furthermore, the relaxed orientation of arms 102 can be such that hooks 104 are positioned under the loop portion so as to inter-connect arms 102 together as the arms 102 become coplanar. Inter-connecting of arms 102 together in this manner can increase the nonlinear deflection characteristic of the arms 102 and/or the electrode 100.

Figure 4A:
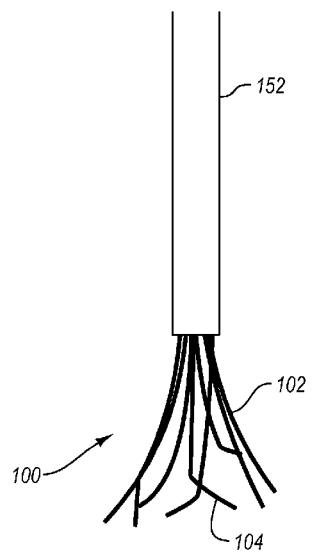
FIG. 4A is a side view of the electrode of FIG. 2 as the electrode is being deployed.
Figure 4B:
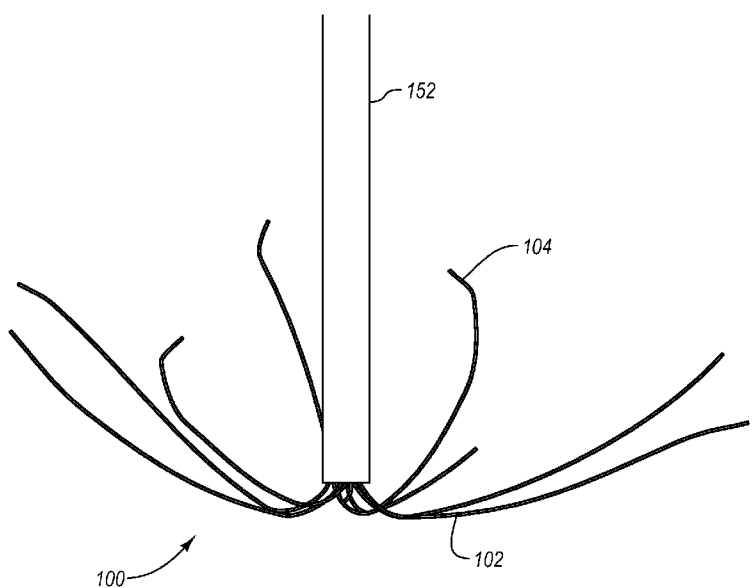
FIG. 4B is a side view of the electrode of FIG. 2 as the electrode is further deployed.
Figure 4C:
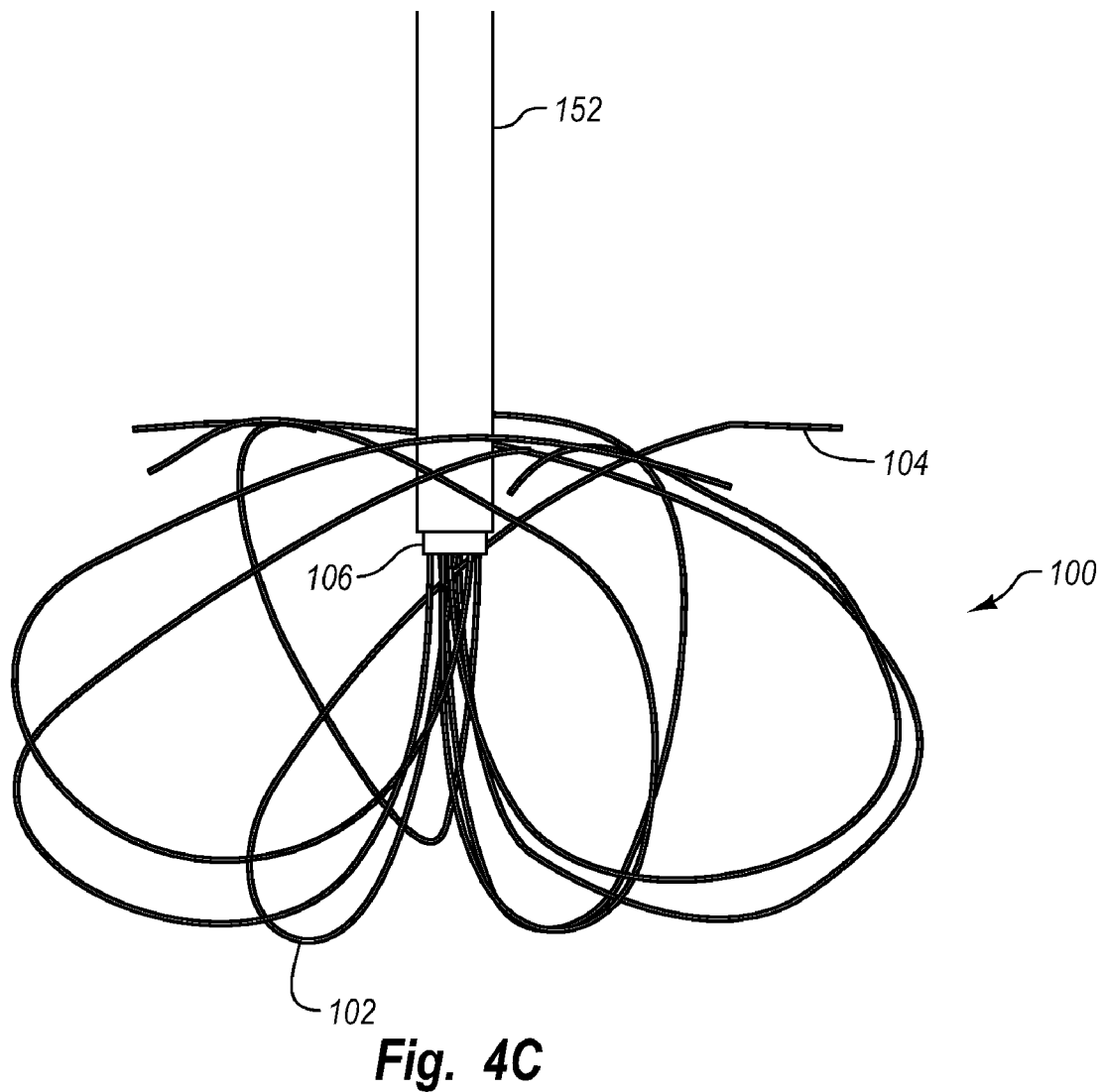
FIG. 4C is a side view of the electrode of FIG. 2 as the electrode is substantially deployed to a trained orientation.

FIGS. 4A to 4C illustrate deployment of electrode 100. With respect to FIG. 4A, a delivery shaft 152, such as a left anchor delivery shaft, is illustrated having arms 102 of electrode 100 extending out therefrom. As shown in the illustration, arms can be positioned within left anchor delivery shaft 152 in a substantially straightened manner. As arms 102 are advanced out of left anchor delivery shaft 152, arms 102 can then begin to return to their relaxed orientation, for example, such as the basket-like shape as illustrated in FIG. 4C. As will be appreciated by one of ordinary skill in the art, because arms 102 are substantially straightened relative to the relaxed orientation as illustrated in FIG. 4C within left anchor delivery shaft 152, electrode 100 can be delivered and/or deployed through a small hole relative to the size of the deployed orientation of electrode 100.

It will be understood by one of ordinary skill in the art in view of the disclosure provided herein that arms 102 can have multiple relaxed orientations. For example, in an alternative embodiment, arms 102 can have a substantially straight first relaxed orientation and a curved second relaxed orientation, wherein respective relaxed orientations are dependent upon a characteristic, such as temperature. It may be desirable to have arms 102 be in a first relaxed orientation while being inserted into a atrium of a patient and thereafter be changed to the second relaxed orientation for positioning against the wall of the atrium.

Electrode 100 can be advanced out of delivery shaft 152 by a variety of means or manners. For example, in one embodiment, the proximal end of housing 106 can be received in the distal end of delivery shaft 152. Housing 106 can then be moved through delivery shaft 152 until the proximal end of housing 106 extends from the proximal end of delivery shaft 152 and arms 102 are received within delivery shaft 152. At this point, housing 106 can be moved distally with respect to delivery shaft 152, thus causing arms 102 to extend from or deploy from delivery shaft 152. Alternatively, arms 102 can extend through delivery shaft 152 and extend out from the proximal end of delivery shaft 152. In this embodiment, the proximal ends of arms 102 can be coupled together so as to maintain the overall shape of electrode 100 as formed by arms 102. The coupled ends of arms 102 can be moved distally with respect to delivery shaft 152 to deploy the trained portions of arms 102.

Arms 102 can be positioned within housing 106 and/or delivery shaft 152 in a manner that enables housing 106 and/or delivery shaft 152 to have a reduced diameter. For example, arms 102 can be configured so as to fit in housing 106 and/or delivery shaft 152 in an organized manner, or in other words substantially reduce overlapping of arms 102. In this manner, the diameter of housing 106 and/or delivery shaft 152 can be reduced. As will be appreciated by one of ordinary skill in the art in view of the disclosure provided herein, the diameter of housing 106 and/or delivery shaft 152 can correspond with the size of the remaining tissue opening after the tissue weld. Accordingly, a smaller diameter of housing 106 and/or delivery shaft 152 can result in a smaller resulting opening after the tissue weld.

Figure 5A:
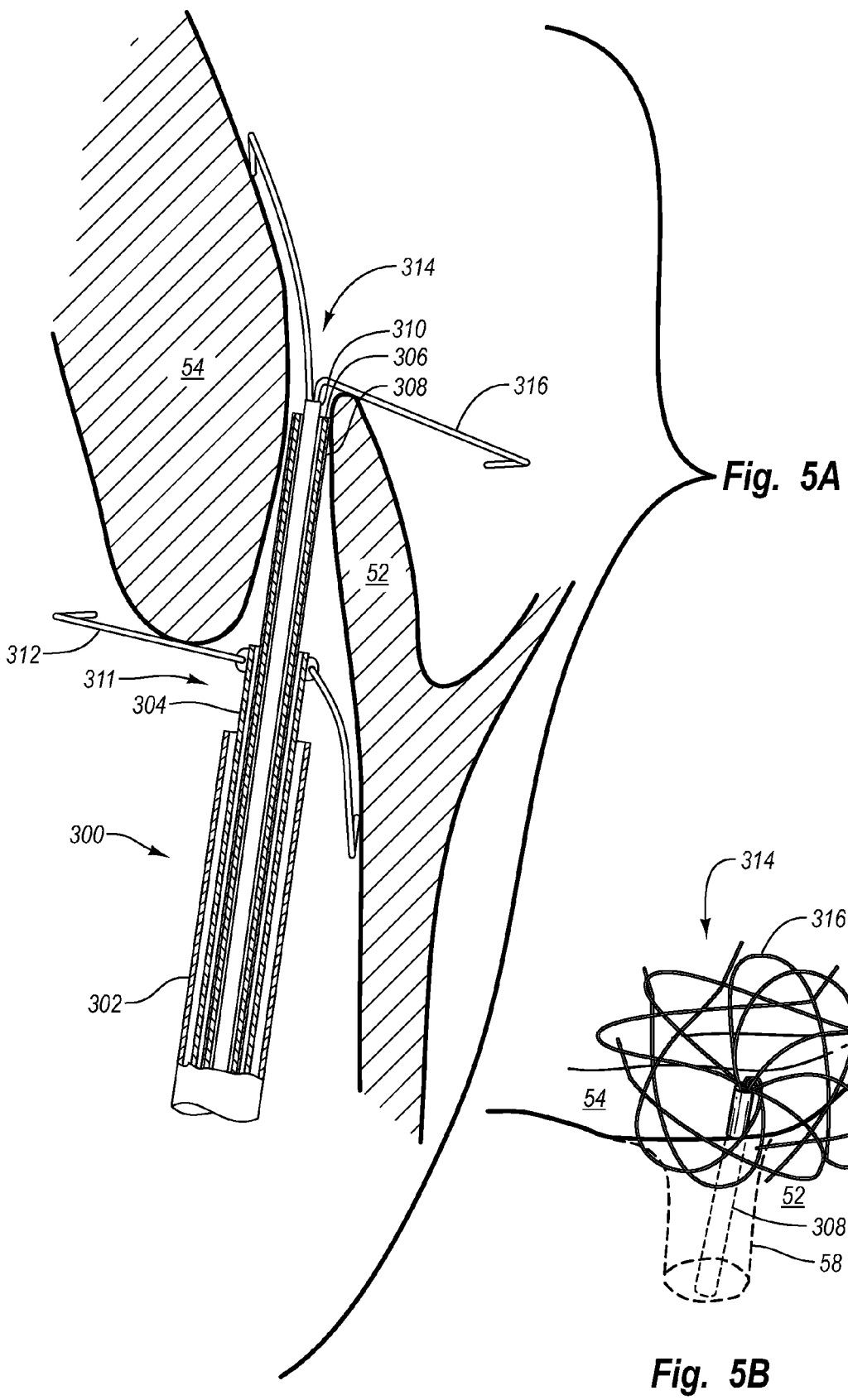
FIG. 5A is a cross-sectional view of the electrode of FIG. 2 in an internal tissue opening.
Figure 5B:
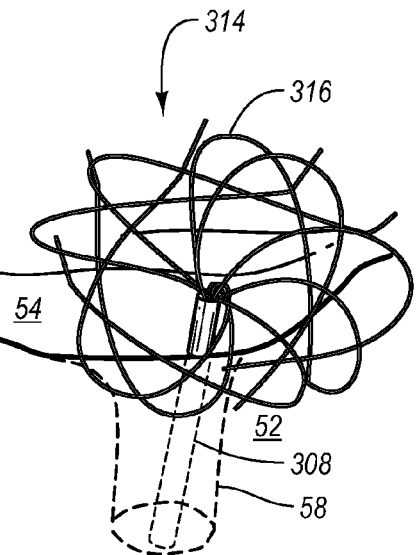
FIG. 5B is a perspective view illustrating the electrode in the left atrium.

FIG. 5A illustrates an example device 300 utilizing an electrode in accordance with the present invention. Furthermore, FIGS. 5A and 5B illustrate the positioning of an electrode in the left atrium of a patient. In the illustrated embodiment, device 300 can include a left electrode 314, a right electrode 311 and a delivery sheath 302 configured to facilitate positioning of left and right electrodes 314, 311. Elements associated with left electrode 314 can include a plurality of shape memory arms 316, a delivery shaft 310 configured to house at least a portion of arms 316, a left electrode delivery tube 306 configured to receive delivery shaft 310 therein, wherein delivery shaft 310 can translate and/or rotate therein, and insulation 308 on the outer surface of left electrode delivery tube 306.

Elements associated with right electrode 311 can include a plurality of shape memory arms 312 and a right electrode catheter 304. In the illustrated embodiment, arms 312 can be coupled to right electrode catheter 304. Furthermore, right electrode catheter 304 can receive left electrode delivery tube 306 therein such that left electrode delivery tube 306 can translate and/or rotate in right electrode catheter 304.

For simplicity of discussion, only two arms 316 of left electrode 314 and two arms 312 of right electrode 311 are illustrated. However, it will be appreciated by one of ordinary skill in the art in view of the disclosure provided herein that left and right electrode can include more than two arms.

As shown in the illustrated embodiment, various elements associated with left electrode 314 can be inserted through the opening of the PFO. For example, delivery shaft 310 and left electrode delivery tube 306 which can enclose at least a portion of left anchor delivery shaft 310, can be received within an opening of the PFO. An approach for transcatheter treatment of a PFO is through the femoral vein and the inferior venacava into the right atrium of the heart. As such, it will be advantageous for the member or electrode that passes through the PFO into the left atrium to have a low crossing profile thus requiring only a small hole to withdraw the device through after the energy delivery and/or "tissue welding" have been accomplished.

In the illustration, delivery sheath 302 can be outside a right electrode catheter 304. When right electrode catheter 304 is extended from delivery sheath 302, right electrode 311 can be deployed such that arms 312 can extend. When right electrode catheter 304 is withdrawn into delivery sheath 302, arms 312 can collapse and enter the right electrode catheter 304.

Left electrode delivery tube 306 can be inside the right electrode catheter 304 and can have insulation 308 in its exterior surface to electrically insulate between the right electrode catheter 304 and the conductive left electrode delivery tube 306 and the conductive delivery shaft 310. Alternatively, insulation can be positioned on the interior surface of left electrode delivery tube 306 or can be positioned on the exterior surface of delivery shaft 310. Furthermore, insulation can be positioned on the interior and exterior surface of left electrode delivery tube 306 and the exterior surface of delivery shaft 310, or any combination thereof.

Delivery shaft 310 can have various shapes, but can be tubular at the distal opening so that left electrode 314 opens radially when deployed. When left electrode 314 is extended from delivery shaft 310, the arms 316 of left electrode 314 can assume their trained or predetermined orientation. When left electrode 314 is withdrawn into delivery shaft 310, arms 316 return to a straightened orientation. In this manner, left electrode 314 can have an increased surface area outside delivery shaft 310 than would otherwise be possible to insert in a patient. In other words, left electrode 314 of the present invention can be pushed out of and pulled back into a tube with a diameter of about 1 mm, for example, and yet expand to a diameter of about 20 mm, for example, and have enough strength to hold the atrial walls together during energy delivery and strongly resist pulling through the PFO.

With arms 312 of right electrode 311 and arms 316 of left electrode 314 being positioned in this manner, energy can be applied to the tissue which is between arms 312 and arms 316. The application of energy in this manner can cause tissue damage. Causing tissue damage in this manner can initiate tissue regrowth so as to weld the tissue together. After such treatment, delivery shaft 310 can be advanced back through the small remaining hole in the PFO and left electrode 314 can be pulled into delivery shaft 310 and left anchor delivery shaft 310 withdrawn without substantially disturbing the weak "tissue weld" that has been created by the procedure.

FIG. 5B illustrates the positioning of electrode 314 against the left atrial wall of the heart. As shown in the illustrated embodiment, electrode 314 is somewhat flattened against the tissue of the heart proximate the opening 58. In this manner, a portion of arms 316 can contact a portion of septum primum 52 and septum secundum 54. As a bottom surface, such as the surface depicted with reference to 108, is pressed against tissue, arms 316 can be configured to collapse so as to form a surface area pattern, such as illustrated in FIG. 5B. More particularly, in one embodiment, withdrawing delivery shaft 310 and arms 316 together can result in arms 316 contacting the underlying tissue. Contact of arms 316 with the underlying tissue can result in the curved portion of arms 316 to flatten. As arms 316 flatten, the contact area between arms 316 and the underlying surface can be increased. The increased contact area can facilitate the application of energy to the underlying tissue to thereby stimulate tissue regrowth.

Figure 6:
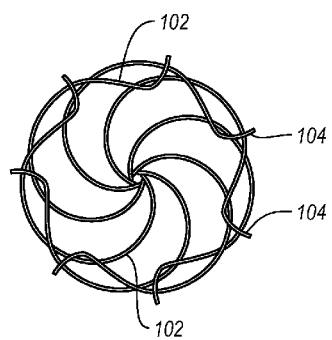
FIG. 6 is a bottom view of an alternative embodiment of an electrode according to the present invention.
Figure 7:
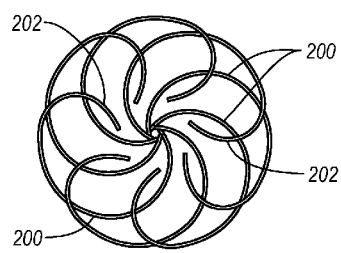
FIG. 7 is a bottom view of an alternative embodiment of an electrode according to the present invention.
Figure 8:
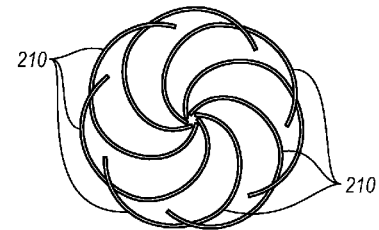
FIG. 8 is a bottom view of an alternative embodiment of an electrode according to the present invention.

FIG. 6 is a bottom view of electrode 100 illustrating the pattern arms 102 may form as arms 102 are flattened by being positioned against tissue. As shown in the illustrated embodiment, hooks 104 are positioned under loop portions of arms 102. As will be appreciated by one of ordinary skill in the art in view of the disclosure provided herein, a variety of types and configurations of electrodes can be utilized without departing from the spirit and scope of the invention. For example, FIG. 7 is a bottom view of an alternative embodiment of an electrode having arms 200. In this embodiment, an inward curve 202 may be utilized. The inward curve 202 may be positioned at the distal ends of arms 200. In this manner, arms 200 may obtain a denser electrode pattern nearer the center of the device. FIG. 8 illustrates yet another embodiment of an electrode having arms 210, wherein arms 210 can extend radially.

It will be understood by one of ordinary skill in the art in view of the disclosure provided herein that while certain embodiments of invention include seven arms, the number of arms can be modified without departing from the spirit and scope of the invention. For example, in one embodiment, electrode includes 10 arms. Alternatively, electrode includes 5 arms. Likewise, the pattern of arm can be modified without departing from the invention.

Figure 9A:
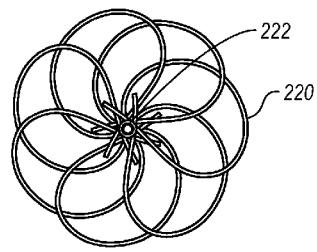
FIG. 9A is a bottom view of an alternative embodiment of an electrode according to the present invention.
Figure 9B:
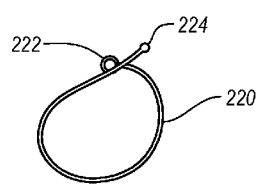
FIG. 9B is a bottom view of the electrode of FIG. 9B.

FIG. 9A illustrates another example of an arm 220 configuration in a left electrode. In this embodiment, the arms 220 can have a predetermined orientation such that arms 220 extend from a delivery shaft 222, curve around and then extend toward and then cross a central axis of the delivery shaft 222. In this manner, extension of the arms 220 can be restrained by delivery shaft 222. FIG. 9B is presented to more clearly illustrate this point with only a single arm 220 depicted to show how arm 220 crosses central axis of delivery shaft 222, such that delivery shaft 222 can constrain arm 220. Furthermore, FIG. 9B illustrates ball 224 being positioned at a distal end of arm 220, it being understood that ball 224 can be implemented into any electrode design disclosed herein.

As illustrated in the figures, embodiments of the invention can utilize larger radius curves in the arms with respect to the delivery shaft. Utilization of a larger radius curve can result in lower stresses and better fatigue characteristics as well as reduced forces required to pull the electrode into a catheter, delivery shaft or housing.

By way of example, a device with 7, 0.008" diameter NiTi arms wrapped with 0.001×0.003 platinum ribbon can be delivered through a tube with a bore of 0.0.037", which is slightly less than 1 mm or 3 French.

One advantage of the invention is that the device can be compliant. The compliancy of the electrode can result in a more even pressure distribution over a potentially irregular surface, such as with the atrial wall at the entrance to the PFO. Furthermore, the compliancy of the electrode can result in the application of substantially even pressure to the atrial wall when the electrode is tilted at an angle to the wall.

The compliance of the electrode has a nonlinear force versus deflection characteristic which can result in the arms becoming stiff as the arms of the electrode become coplanar. This can provide to the user a tactile feel that the device is engaged against the atrial tissue. Furthermore, the compliancy of the electrode can reduce the likelihood of the electrode inadvertently being pulled through the PFO during use.

The present invention may be embodied in other specific forms without departing from its spirit or essential characteristics. The described embodiments are to be considered in all respects only as illustrative and not restrictive. Exemplary claims have been included herein to illustrate embodiments of the invention. Although exemplary claims are presented, the invention is not limited to these claims, and the applicant reserves the right to present different or other claims in the future in view of the embodiments of the invention described herein.

What is claimed is:

1. A PFO closure device, comprising:
    a left electrode comprising a plurality of conductive wires formed of a shape memory material, wherein:
    the wires having a trained portion, the trained portion having a relaxed orientation;
    the trained portion of the wires are configured to be restrained within a left anchor delivery shaft in a straight orientation for delivery into a patient, but thereafter can return to the relaxed orientation after free ends of the wires extend from the delivery shaft; and
    upon being deployed into a left atrium of a patient and thereby becoming unrestrained from the delivery shaft, the wires assume their relaxed orientation wherein each wire engages at least one adjacent wire such that the wires are interconnected, and wherein the relaxed orientation is such that the wires extend outward away from a central axis of the delivery shaft, curve back around toward the central axis of the delivery shaft and then cross over and extend beyond the central axis of the delivery shaft;
    a left electrode delivery tube in electrical communication on an inner surface with the delivery shaft; and
    a right electrode catheter encompassing the left electrode delivery tube, the right electrode catheter being in communication with a right electrode such that current can be applied across tissue separating the left electrode and the right electrode, thereby damaging the tissue and generating tissue regrowth.

2. A device as recited in claim 1, wherein the wires are configured such that applying a retracting force to the wires with respect to the left anchor delivery shaft will retract the trained portion of the wires into the left anchor delivery shaft.

3. A device as recited in claim 1, wherein the trained portion is configured such that retracting the wires and left anchor delivery shaft with respect to the tissue defining the PFO opening causes the trained portion of the wires to flatten against the tissue.

4. A device as recited in claim 1, wherein the right electrode includes another plurality of wires.

5. A device as recited in claim 1, further comprising electrical insulation positioned on an outer surface of the left electrode delivery tube.

6. A device as recited in claim 1, further comprising a delivery sheath enclosing at least a portion of the right electrode catheter.

7. A device as recited in claim 1, wherein the trained portion has a second relaxed orientation different than the first relaxed orientation.

* * * * *